United States Patent
Qing et al.

(10) Patent No.: US 12,089,913 B2
(45) Date of Patent: Sep. 17, 2024

(54) MONITORING SYSTEM, DATA TRANSMISSION METHOD, PORTABLE MONITOR, AND CONFIGURATOR

(71) Applicants: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(72) Inventors: Lei Qing, Shenzhen (CN); Wenjun Liu, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD, Shenzhen (CN)

(*) Notice: Subject to any disclaimer, the term of this patent is extended or adjusted under 35 U.S.C. 154(b) by 1207 days.

(21) Appl. No.: 16/652,002

(22) PCT Filed: Sep. 30, 2017

(86) PCT No.: PCT/CN2017/105177
§ 371 (c)(1),
(2) Date: Jul. 10, 2020

(87) PCT Pub. No.: WO2019/061548
PCT Pub. Date: Apr. 4, 2019

(65) Prior Publication Data
US 2020/0345233 A1   Nov. 5, 2020

(51) Int. Cl.
*A61B 5/00* (2006.01)
*A61B 5/0205* (2006.01)
(Continued)

(52) U.S. Cl.
CPC ........ *A61B 5/0022* (2013.01); *A61B 5/02055* (2013.01); *A61B 5/7445* (2013.01); *A61B 5/746* (2013.01); *A61B 2560/0431* (2013.01)

(58) Field of Classification Search
CPC ... A61B 5/02055; A61B 5/7445; A61B 5/746; G16H 40/63; G16H 40/67; G16H 40/40; H04W 4/33
(Continued)

(56) References Cited

U.S. PATENT DOCUMENTS

| | | | |
|---|---|---|---|
| 5,752,917 A | 5/1998 | Fuchs | |
| 5,936,539 A * | 8/1999 | Fuchs | G16H 40/67 455/100 |

(Continued)

FOREIGN PATENT DOCUMENTS

| | | |
|---|---|---|
| CN | 102110190 A | 6/2011 |
| CN | 102160819 A | 8/2011 |

(Continued)

OTHER PUBLICATIONS

Extended European Search Report issued in related European Application No. 17926625.9, mailed Apr. 1, 2021, 8 pages.
(Continued)

*Primary Examiner* — Maria El-Zoobi
(74) *Attorney, Agent, or Firm* — BAYES PLLC

(57) ABSTRACT

A monitoring system, a data transmission method, a portable monitor, and a configurator. The system includes the portable monitor and the configurator; a mechanical detachable connection can be realized between the portable monitor and the configurator; the portable monitor is configured to work independently after the two are mechanically separated. The configurator is used for storing description information. The portable monitor includes a measurement module for collecting physiological data of a patient; a communication
(Continued)

module for accessing to a network for a hospital and transmitting the physiological data; a connection detection circuit for outputting a control signal after detecting that the portable monitor is connected to the configurator; a processor for obtaining the description information from the configurator, and configuring the portable monitor according to the description information.

10 Claims, 4 Drawing Sheets

(58) Field of Classification Search
USPC ..................................................... 379/106.02
See application file for complete search history.

(56) References Cited

U.S. PATENT DOCUMENTS

| | | | |
|---|---|---|---|
| 2005/0033124 A1 | 2/2005 | Kelly et al. | |
| 2007/0135866 A1* | 6/2007 | Baker | A61B 5/1113 600/407 |
| 2008/0243020 A1 | 10/2008 | Chou | |
| 2010/0280339 A1* | 11/2010 | Russ | A61B 5/0205 128/903 |
| 2011/0047298 A1 | 2/2011 | Eaton et al. | |
| 2011/0090086 A1 | 4/2011 | Dicks et al. | |
| 2012/0317327 A1* | 12/2012 | Eaton | G16H 40/63 710/303 |
| 2013/0046197 A1 | 2/2013 | Bishop et al. | |
| 2013/0109927 A1* | 5/2013 | Menzel | A61B 5/002 600/300 |
| 2014/0188516 A1 | 7/2014 | Kamen et al. | |
| 2014/0379369 A1* | 12/2014 | Kokovidis | G16H 40/67 705/2 |
| 2015/0297079 A1 | 10/2015 | Tateda et al. | |
| 2018/0103874 A1* | 4/2018 | Lee | A61B 5/6823 |

FOREIGN PATENT DOCUMENTS

| | | |
|---|---|---|
| CN | 202211751 U | 5/2012 |
| CN | 102949243 A | 3/2013 |
| CN | 103690159 A | 4/2014 |
| CN | 104107088 A | 10/2014 |
| CN | 204562150 U | 8/2015 |
| WO | 2008056033 A1 | 5/2008 |

OTHER PUBLICATIONS

First Office Action issued in related Chinese Application No. 201780095153.0, mailed May 23, 2022, 9 pages.
International Search Report issued in corresponding International Application No. PCT/CN2017/105177, mailed Jun. 15, 2018, 4 pages.
EP Com Art 94(3) issued in related European Application No. 17926625.9, mailed Mar. 15, 2024, 5 pages.

* cited by examiner

MONITORING SYSTEM, DATA TRANSMISSION METHOD, PORTABLE MONITOR, AND CONFIGURATOR

CROSS-REFERENCE TO RELATED APPLICATIONS

This application is a U.S. national phase application of PCT Application No. PCT/CN2017/105177, filed Sep. 30, 2017, entitled "MONITORING SYSTEM, DATA TRANSMISSION METHOD, PORTABLE MONITOR, AND CONFIGURATOR," the entire contents of which are incorporated herein by reference.

TECHNICAL FIELD

This disclosure relates to the field of computer technology, and particularly to a monitoring system, a data transmission method, a portable monitor and a configurator.

BACKGROUND

With the development of computer technology, the computer technology is more and more widely used in the medical field. At present, during the hospitalization of a patient, due to changes in the patient's condition, it is often necessary to transfer the patient among different wards, departments or inpatient areas, where portable patient monitors are used for monitoring the patient to ensure the safety thereof during the transfer of the patient. When the patient monitored by the portable patient monitor reaches a new ward, department or inpatient area, and is kept to be monitored by the portable patient monitor, it is generally necessary to perform some settings on the portable patient monitor according to the conditions of the new ward, department or inpatient area, for example, to reset department information and/or bed number information of the portable patient monitor, to reconnect to a central station of the new department and upload patient data, to reconnect to a printer of the new department to facilitate subsequent report printing.

At present, in addition to manually setting those information, the main solution includes replacing the portable patient monitor after reaching the new department, but this solution cannot upload the data of the patient before and during the transfer to the central station of the new department. Next, a portable patient monitor for transfer is directly used as a module of a bedside portable patient monitor of the new department, but this solution requires a fixed portable patient monitor at the bedside. For some patients who are less ill, using an additional portable patient monitor at the bedside will bring additional costs. Finally, the settings corresponding to different wards, departments or inpatient areas are preset in the portable patient monitor and saved as configurations, but this solution requires that the portable patient monitor has a large enough storage.

SUMMARY OF THIS DISCLOSURE

In a first aspect, a monitoring system can be provided in embodiments of this disclosure, which may include a portable patient monitor and a configurator. The portable patient monitor and the configurator may be in a detachable mechanical connection with each other, and the portable patient monitor is capable of working independently after the portable patient monitor and the configurator are mechanically separated.

The configurator may be used for storing description information that at least include one of network configuration information and medical area position setting information The portable patient monitor may include:
a measurement module that may collect physiological data of a patient;
a communication module that may have access to a network for a hospital and performs data transmission of the physiological data;
a first connection detection circuit that is capable of outputting a control signal after detecting that the portable patient monitor is connected to the configurator; and
a processor that may obtain the description information from the configurator based on the control signal, and configure the portable patient monitor according to the obtained description information.

In a second aspect, a data transmission method that may be used in a portable patient monitor may be provided in embodiments of this disclosure, including:
obtaining description information including network configuration information and medical area position setting information;
performing network configuration according to the network configuration information in the description information, and accessing to a network device in a network for a hospital; and
sending physiological data and the medical area position setting information to the network device in the network for a hospital when the collected physiological data needs to be sent to a server.

In a third aspect, a data transmission method that may be used in a configurator may be provided in embodiments of this disclosure, including:
outputting a control signal when the configurator is detected to be connected with a power interface of a portable patient monitor; and
sending stored description information of a target object to the portable patient monitor based on the control signal.

In a fourth aspect, a portable patient monitor may be provided in embodiments of this disclosure, which may include a data interface, a processor and a memory, the data interface, the processor and the memory being interconnected.

The memory may be used for storing a computer program that includes program instructions, and the processor may be configured to invoke the program instructions to perform the following steps:
obtaining description information, the description information comprising network configuration information and medical area position setting information;
performing network configuration according to the network configuration information in the description information, and accessing to a network device in a network for a hospital; and,
sending physiological data and the medical area position setting information to a network device in the network for a hospital when the collected physiological data needs to be sent to a server.

In a fifth aspect, a configurator may be provided in embodiments of this disclosure. The configurator may include a data interface, a processor and a memory, where the data interface, the processor and the memory being interconnected.

The memory can be used for storing a computer program that includes program instructions, and the processor can be configured to invoke the program instructions to perform the following steps:

outputting a control signal when the configurator is detected to be connected with a power interface of a portable patient monitor; and sending description information to the portable patient monitor based on the control signal, wherein the description information comprises at least one of network configuration information and medical area position setting information.

In a sixth aspect, another portable patient monitor may be provided in embodiments of this disclosure. The portable patient monitor may include:

a measurement module that may collect physiological data of a patient;

a communication module that may have access to a network for a hospital and perform data transmission of the physiological data; and, a first connection detection circuit that is capable of outputting a control signal after detecting that the portable patient monitor has been connected to a configurator, wherein the configurator and the portable patient monitor can be mechanically separated; and a processor that may obtain description information from the configurator based on the control signal, and perform configuration on the portable patient monitor according to the obtained description information, wherein the description information may include at least one of network configuration information and medical area position setting information.

In the embodiments of this disclosure, the portable patient monitor can obtain the description information, perform network configuration according to the network configuration information in the description information, and further access to a central server or a server, and when the collected physiological data needs to be transmitted to the central server or the server, the physiological data and the medical area position setting information can be transmitted to the central server or the server, thereby achieving rapid configuration of the portable patient monitor.

BRIEF DESCRIPTION OF THE DRAWINGS

Following detailed descriptions of respective embodiments in this disclosure can be understood better when combining with these figures, in which the same structure is represented by the same reference sign. In the figures.

DETAILED DESCRIPTION

Figure 1A:
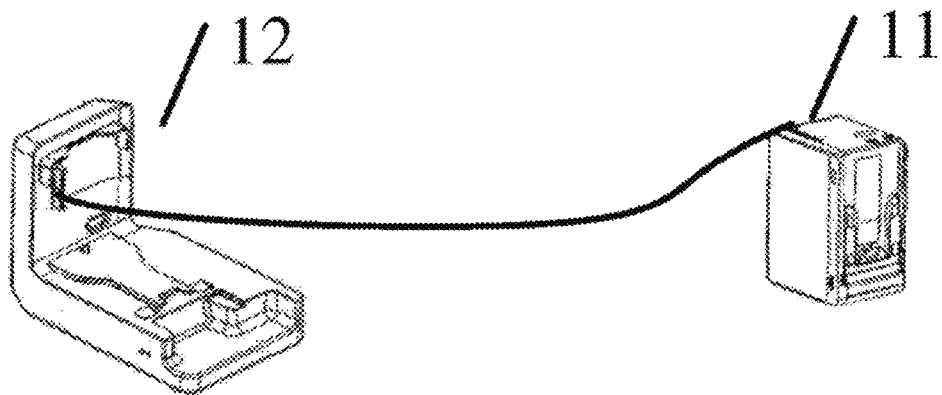
FIG. 1a is a schematic structural diagram of a monitoring system provided by an embodiment of this disclosure.

The technical solutions of the embodiments of this disclosure will be described below clearly and comprehensively with reference to the drawings of the embodiments of this disclosure. Obviously, the embodiments described below are merely some of the embodiments of this disclosure, rather than all the possible embodiments. Based on the embodiments in this disclosure, all the other embodiments that can be obtained by those of ordinary skilled persons in the art without any inventive effort shall fall within the scope of protection of this disclosure.

Some embodiments of this disclosure will be further described in detail below with reference to the drawings. In the case of no conflict, the embodiments and the features thereof described below can be combined with each other.

This disclosure provides a monitoring system that may include a portable patient monitor and a configurator, and may be mainly used in the medical field. The monitoring system can achieve rapid and effective configuration of the portable patient monitor, improve the efficiency, accuracy and convenience in setting the portable patient monitor, and ensure effective and accurate transmission of the information of the patient(s) within the hospital by the configuration below: the configurator may store description information, and the portable patient monitor may establish a connection with the configurator, obtain the description information stored in the configurator, and perform network configuration and/or set medical area position information for the portable patient monitor according to the obtained description information.

The description information described herein may include at least one of network configuration information and medical area position setting information. The network configuration information can be used for enabling the portable patient monitor to access to a network for a hospital, and the medical area position setting information can be used for enabling the portable patient monitor to perform data transmission of physiological data to some servers and other devices within the hospital.

In one embodiment, the portable patient monitor may include: a measurement module, a communication module, a first connection detection circuit and a processor. For the portable patient monitor, the measurement module can be operated to collect physiological data of a patient (the patient mentioned here may refer to any person whose physiological data is obtained using the measurement module), the first connection detection circuit can output a control signal after detecting that the portable patient monitor has been connected to the configurator, and the processor can obtain the description information from the configurator according to the control signal and configure the portable patient monitor according to the obtained description information. The configuration here may include network configuration based on network configuration information. After the network configuration, a network may be established between the portable patient monitor and a central server, a printer and other devices, and the communication module may implement data transmission of the physiological data with a network transmission node in a network for a hospital in a wired or wireless manner. In some embodiments, the configuration here may also include information setting about the position where a medical area is located based on medical area position setting information. Accordingly, the portable patient monitor can be quickly associated and bound with partition setting information of the patient based on the information setting. For example, ward identification, department identification or hospital region related setting information, hospital bed identification and other information can be pre-stored in the configurator fixed at the bedside, the portable patient monitor can directly read the stored information from the configurator to complete loading and configuration of ward, department, hospital bed or hospital region related setting information, and quickly change the setting of the corresponding information. The detection of whether the portable patient monitor is connected to the configurator may be achieved by detecting that whether a wireless connection is established between the portable patient monitor and the configurator based on network communication, or by detecting that whether a mechanical connection is established between the portable patient monitor and the configurator. The mechanical connection may include that the portable patient monitor and the configurator may be fixed via a sliding groove, or may be connected via one or more hardware interfaces.

The network configuration information described herein may include access information, such as a network type and/or an IP address. The portable patient monitor may perform the network configuration and access to the network for the hospital according to the network type and/or the IP address described in the access information, where the portable patient monitor may access to a part of the network for the hospital that is related to the medical area position setting information in one of the embodiments. The network configuration information may further include an IP address of a central server. The portable patient monitor may perform connection configuration and further access to the central server in the medical network according to the obtained IP address of the central server. In one embodiment, the central server may be a server related to the medical area position setting information. The network configuration information may further include an IP address of a printer. The portable patient monitor may perform configuration and further connect to the printer in the medical network according to the obtained IP address of the printer. In one embodiment, the printer connected with the portable patient monitor may be related to the medical area position setting information.

The medical area position setting information described herein may be one or more of bed number identification, department identification, disease section identification and ward identification. The network for the hospital may be divided into multiple network parts according to the department, the hospital region, the bed number, the ward, and each network part may correspond to a different central server, printer, server, network transmission node, etc. In this way, when the portable patient monitor obtains the corresponding medical area position setting information from the configurator, it can also automatically read the corresponding network configuration information to complete the network connection configuration.

The portable patient monitor described herein may be a monitor that can be moved inside the hospital. The network for the hospital described herein may be a wired network or a wireless network. The wired network is a network architecture built by connecting to a server or a central server through a network cable. The wireless network may be a wireless network architecture built based on one or more of Bluetooth transmission, WiFi network transmission and infrared radio frequency transmission, etc. The server or the central server described herein may be one of nurse stations and hospital-level servers of the various departments.

In one embodiment, the processor in the portable patient monitor may receive the physiological data obtained from the measurement module, and process the physiological data to obtain a physiological parameter information value, physiological parameter waveform data, physiological parameter trend waveform data, alarm data, an alarm prompt information, a trend alarm information, early warning data, etc., for displaying and/or prompting the data. The data obtained by the portable patient monitor based on the physiological data may be transmitted to a bedside patient monitor through the network for the hospital for displaying and/or prompting, or may be transmitted to the server or the central server through the network for the hospital for displaying and/or prompting.

In one embodiment, the communication module in the portable patient monitor may upload a data packet to the network for the hospital, and the data packet may include one or more of the following data for displaying and/or prompting including physiological parameter information value, the physiological parameter waveform data, the physiological parameter trend waveform data, the alarm data, the alarm prompt information, the trend alarm information, and the early warning dat. The network for the hospital may include a network that communicates with a bedside patient monitor beside the hospital bed, and one of networks that communicate with the server or the central server.

Referring to FIG. 1a, FIG. 1a is a schematic structural diagram of a monitoring system provided by an embodiment of this disclosure. The system may include: a portable patient monitor 11 and a configurator 12, where a mechanical detachable connection can be realized between the portable patient monitor 11 and the configurator 12. The portable patient monitor is capable of working independently after the portable patient monitor 11 and the configurator 12 are mechanically separated. The portable patient monitor 11 may be provided with a touch screen.

A battery module may be provided on the portable patient monitor 11 or the configurator 12, an external power interface may be provided on the portable patient monitor 11, and the configurator 12 may be provided with a first power interface and a second power interface. The second power interface can be connected to the first power interface. When the battery module is provided on the portable patient monitor 11 or the configurator 12, the second power interface may also be connected to the battery module.

In one embodiment, the configurator 12 may be connected to the commercial power via the first power interface, and may be connected to the external power interface provided on the portable patient monitor via the second power interface. The configurator 12 may use a second connection detection circuit to detect whether the second power interface is connected with the external power interface and the second connection detection circuit may output the control signal when it is detected that the second power interface has been connected with the external power interface. If the control signal is output after the second connection detection circuit detects that the portable patient monitor is connected to the configurator, the portable patient monitor 11 may obtain the description information from the configurator 12 according to the control signal, and the portable patient monitor 11 may be configured according to the description information. After the network configuration is completed, the portable patient monitor 11 may use the communication module to establish a wired or wireless communication connection with the central server or the server, the printer, etc. The portable patient monitor 11 can use the communication module to transmit the physiological data and the medical area position setting information.

In one embodiment, the monitoring system may use the configurator 12 to collect the physiological data of the patient, where the physiological data may include one or more of electrocardiogram, blood oxygen, respiration, body temperature, blood pressure.

In one embodiment, the portable patient monitor 11 is a device or a system that can measure and control the physiological data of the patient, compare the physiological data with one or more set values, and issue an alarm if the physiological data is out of range. The portable patient monitor 11 may be fixed beside the hospital bed or fixed inside the ward, a transferable portable patient monitor or a central portable patient monitor. The configurator 12 includes, but is not limited to, an external device with a storage function, such as a docking station configurator and a USB flash drive, where the configurator may be a base for extending the function of a terminal device, and can be connected to a variety of external devices, such as a driver, a large-screen display, a keyboard, a printer and a scanner via interfaces and slots. The portable patient monitor 11 may establish a communication connection with the configurator 12 in a wired or wireless manner. The configurator 12 may be used for storing the description information. The portable patient monitor 11 may be used for obtaining the description information stored in the configurator when the connection between the portable patient monitor and the configurator is established, and configuring the portable patient monitor according to the obtained description information. The central server or the server may be one or more central servers; for example, the central server or the server may be a central station of a certain nurse station in the hospital.

In one embodiment, the network configuration information may include network channel configuration information for communicating with a bedside patient monitor; and the processor may obtain the network channel configuration information from the configurator based on the control signal, and configure the communication module of the portable patient monitor according to the obtained network channel configuration information, thereby establishing a communication channel with the bedside patient monitor. In other embodiments, the connection detection circuit, i.e., the second connection detection circuit, described herein may also be provided on the configurator.

Figure 1B:
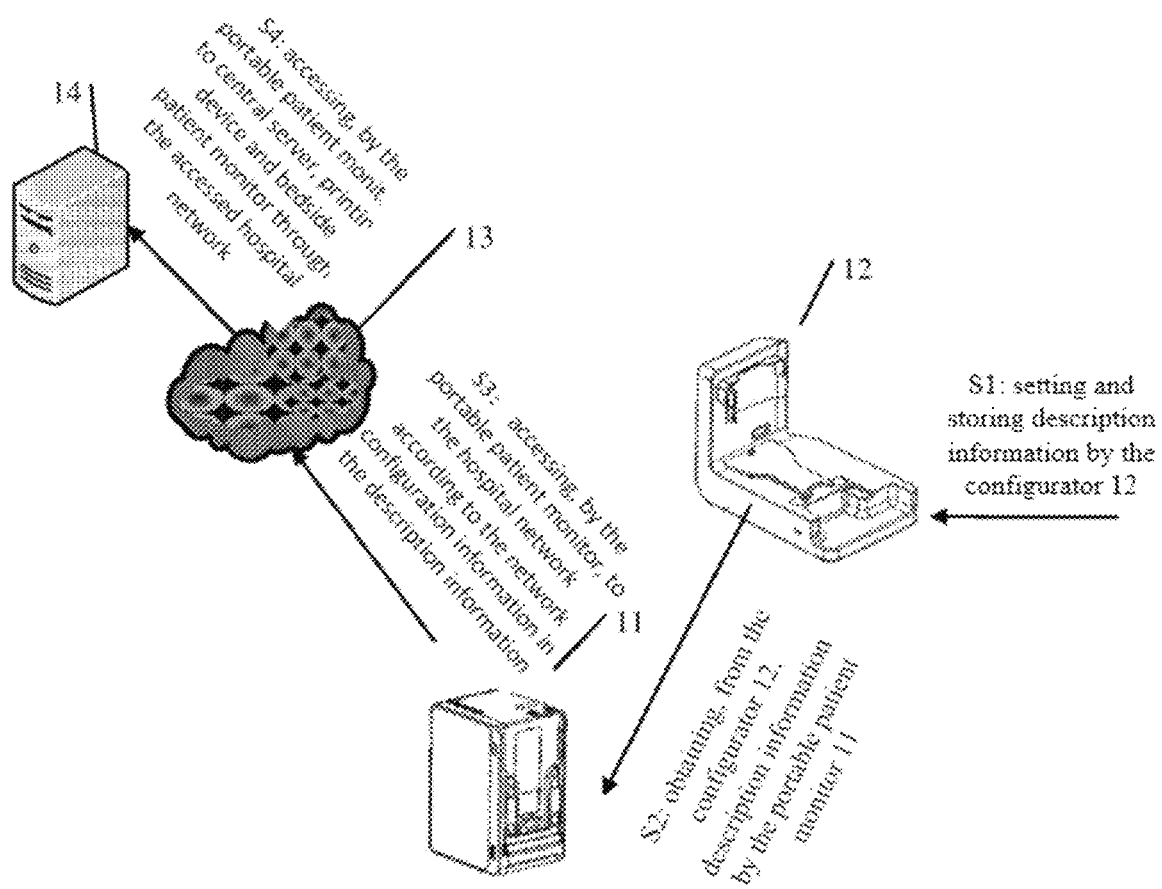
FIG. 1b is a schematic structural diagram of another monitoring system provided by an embodiment of this disclosure.

Referring to FIG. 1b, FIG. 1b is a schematic structural diagram of another monitoring system provided by an embodiment of this disclosure. As shown in FIG. 1b, the monitoring system may include a portable patient monitor 11, a configurator 12, a wired or wireless network 13, and a central server or a server 14, and the monitoring system may mainly complete the configuration of the portable patient monitor through the following steps.

At step S1, the configurator 12 can set and store description information. The description information stored in the configurator 12 may be uniformly distributed and updated through the network for the hospital, individually updated and set by medical staff, or updated by means of a sub-communication module, communicating with a bedside patient monitor, provided in the configurator 12. After the bedside patient monitor establishes communication with the configurator 12, the description information in the configurator can be changed or set by the bedside patient monitor. When the sub-communication module is provided in the configurator 12, settings or change message of the description information transmitted from the bedside patient monitor or any network connection node in the medical network can be periodically received, so as to change or set the description information stored in the configurator 12 according to the received settings or change messages.

At step S2, the portable patient monitor 11 may obtain the description information from the configurator 12.

In an embodiment of this disclosure, the description information may include network configuration information and medical area position setting information. The network configuration information may include one or more of the network type and/or the IP address described, the IP address of the central server, and the IP address of the printer. The medical area position setting information may be one or more of bed number identification, department identification, hospital region identification, and ward identification.

At step S3, the portable patient monitor 11 may access to the network for the hospital to which it belongs according to access information of the network configuration information in the obtained description information.

In an embodiment of this disclosure, the portable patient monitor 11 may access to the network for the hospital to which it belongs according to the network type and/or the IP address described in the obtained description information. The portable patient monitor may use the medical area position setting information for determining the network for the hospital to which it belongs.

For example, in one of the embodiments, the portable patient monitor 11 may access to a part of the network for the hospital that is related to the medical area position setting information according to the access information of the network configuration information in the obtained description information. For example, the portable patient monitor 11 may access to a part of the network for the hospital that corresponds to one of the bed number identification, the department identification, the hospital region identification, the ward identification, etc. For example, in one of the embodiments, the portable patient monitor may perform connection configuration according to the obtained IP address of the central server, and access to the server related to the medical area position setting information in the network for the hospital, where the server related to the medical area position setting information may be a server corresponding to one of the bed number identification, the department identification, the hospital region identification, the ward identification, etc., such as a server corresponding to the hospital region, or a server corresponding to the department. For example, in one of the embodiments, the portable patient monitor may perform configuration according to the obtained IP address of the printer, and connect to a printer related to the medical area position setting information in the medical network. The printer related to the medical area position setting information may be a printer corresponding to one of the bed number identification, the department identification, the hospital region identification and the ward identification, etc., such as a printer corresponding to the hospital region, a printer corresponding to the department, and a printer corresponding to the hospital bed.

At step S4, the portable patient monitor may access to the central server, the printing device (such as the printer), the bedside patient monitor, etc. through the accessed network for the hospital. When the portable patient monitor is automatically connected to the bedside machine, the network configuration information in the description information may include communication channel configuration information of a bedside patient monitor. For example, when the bedside patient monitor uses a wireless connection, the network configuration information in the description information may contain frequency setting information, frequency band and authentication key for wireless communication with the bedside patient monitor.

The portable patient monitor may access, through the accessed network for the hospital, to the central server according to the IP address of the central server.

After the above configuration step, the portable patient monitor may collect the physiological data in real time or manually, and the collected physiological data of the patient and the obtained medical area position setting information including the bed number identification or including the bed number identification and the department identification can be sent to the accessed central server or the server through the accessed network for the hospital, so as to achieve fast and efficient data transmission.

The monitoring system provided by an embodiment of this disclosure can include the portable patient monitor 11 and the configurator 12, where the configurator 12 may include an external device with a storage function, such as a configurator and a USB flash drive. In one embodiment, the monitoring system can include the portable patient monitor and the configurator, where a storage chip can be provided in the configurator. After the portable patient monitor establishes a communication connection with the configurator, the storage chip can be read and written. The configurator is installed beside each hospital bed in each ward, each department or each hospital region, and the installed configurator belongs to the department and generally does not need to be moved. After the portable patient monitor establishes a communication connection with the configurator, the description information related to the ward, department or hospital region (such as the medical area position setting information (department, bed number, etc.) of the portable patient monitor, target central server connection information (name, IP address, etc., of the central server to be connected), network configuration (IP address, network type, etc.), printer connection information (name, IP address, etc., of the printer), default configuration information of department, etc.) can be stored in the storage chip of the configurator. When the patient monitored by any portable patient monitor arrives at the bedside, after the portable patient monitor is connected to the configurator, the portable patient monitor may read related setting information from the storage chip in the configurator, automatically load the related setting information and complete the settings.

In one embodiment, the description information stored in the configurator 12 of the monitoring system may include network configuration information including access information, and the portable patient monitor 11 may obtain the description information stored in the configurator 12 by establishing the communication connection with the configurator 12. The portable patient monitor 11 may perform network configuration and access to the network for the hospital according to the network type and/or the IP address described in the access information of the network configuration information in the obtained description information. It is noted that the portable patient monitor 11 can establish the communication connection with the configurator 12 in a wired or wireless manner, which is not limited in the embodiments of this disclosure. The embodiments of this disclosure do not limit the manner in which the portable patient monitor 11 accesses to a data network of a target area.

In one embodiment, the network configuration information in the description information stored in the configurator 12 of the monitoring system may include the IP address of the central server, and the portable patient monitor 11 can obtain the IP address of the central server in the network configuration information in the description information stored in the configurator 12 by establishing the communication connection with the configurator 12. The portable patient monitor 11 may perform connection configuration according to the obtained IP address of the central server, and access to the central server or the server related to the medical area position setting information.

In one embodiment, the network configuration information in the description information stored in the configurator 12 of the monitoring system may also include the IP address of the printer, and the portable patient monitor 11 may obtain the IP address of the printer in the network configuration information in the description information stored in the configurator 12 by establishing the communication connection with the configurator 12. The portable patient monitor 11 may perform configuration according to the obtained IP address of the printer, and accesses to a printer related to the medical area position setting information.

In one embodiment, the target object may include a hospital bed in a target area, and the description information may further include medical area position setting information. The medical area position setting information may include bed number identification, or the medical area position setting information may include bed number identification and department identification. After establishing the communication connection with the configurator 12 and completing the configuration, when the collected physiological data of the patient (target object) needs to be sent to the central server or the server, the portable patient monitor 11 can send the physiological data and the medical area position setting information to the central server or the server.

In an embodiment of this disclosure, the monitoring system may store the description information of the target object in the target area through the configurator 12, obtain the description information stored in the configurator 12 through the connection between the portable patient monitor 11 and the configurator 12, and realize the network configuration of the portable patient monitor 11 according to the obtained description information of the target object in the target area, thereby improving the setting efficiency and accuracy of the portable patient monitor, and simplifying the user's operation.

Figure 2:
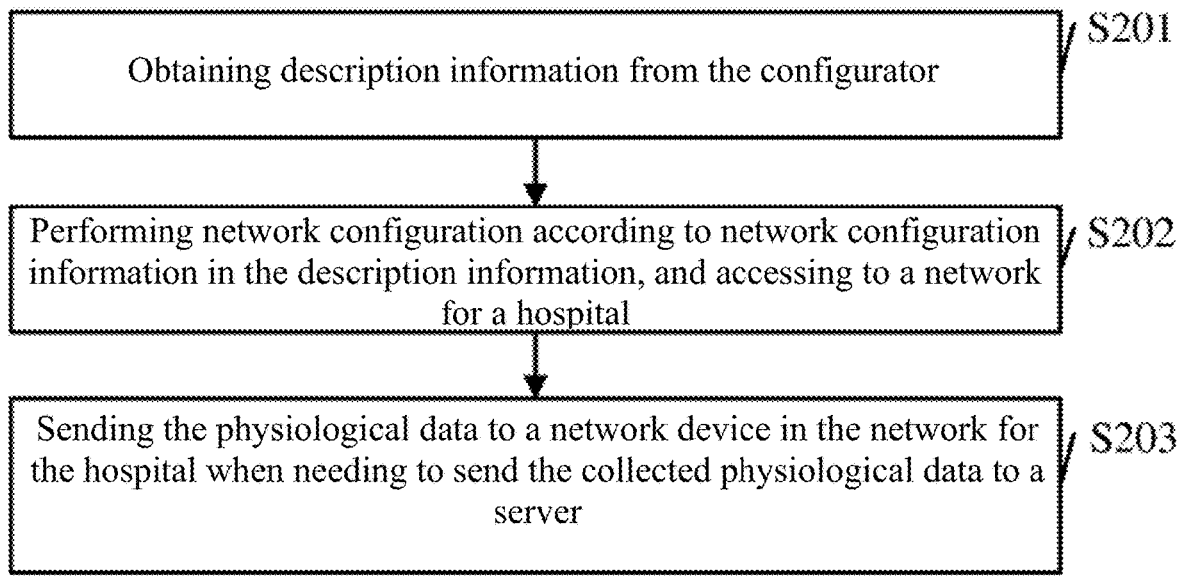
FIG. 2 is a schematic flowchart of a data transmission method provided by an embodiment of this disclosure.

Specifically, referring to FIG. 2, FIG. 2 is a schematic flow chart of a data transmission method provided by an embodiment of this disclosure. The method may be performed by a portable patient monitor, which is provided in a monitoring system, where the monitoring system may include the portable patient monitor and a configurator. The specific explanations of the portable patient monitor and the configurator are as previously described. Specifically, the method of the embodiment of this disclosure may include the following steps.

At step S201, description information may be obtained from the configurator independent of the portable patient monitor.

In an embodiment of this disclosure, the portable patient monitor may obtain the description information. The description information may include medical area position setting information. The medical area position setting information may include bed number identification, or the medical area position setting information may include bed number identification and department identification. Specifically, the portable patient monitor may establish a communication connection with the configurator provided inside a ward or beside a hospital bed in a wired or wireless manner. The portable patient monitor may obtain the medical area position setting information including the bed number identification or including the bed number identification and the department identification in the description information of a target object in a target area that is stored in the configurator. For example, the portable patient monitor may be inserted into the configurator of the hospital bed in the target area in a wired manner. The configurator may include a storage chip in which description information of the hospital bed in the target area is stored, wherein the description information may include network configuration information and/or medical area position setting information, and the medical area position setting information may include the bed number identification of the hospital bed in the target area, or the medical area position setting information may include the bed number identification and the department identification of the hospital bed in the target area. In an example, after the portable patient monitor establishes the connection with the configurator, the obtained medical area position setting information of the hospital bed in the target area is a bed number of 51 and a department of 02, i.e. endocrine department.

At step S202, network configuration may be performed according to the network configuration information in the description information, and the portable patient monitor can further access to a network for a hospital.

In an embodiment of this disclosure, the portable patient monitor may establish a connection with the configurator provided inside a ward or beside a hospital bed, obtain the description information stored in the configurator, then perform network configuration according to the network configuration information in the description information, and access to a central server or a server in the network for the hospital (such as the central server). Specifically, the portable patient monitor may establish the communication connection with the configurator provided inside the ward or beside the hospital bed in a wired or wireless manner, and obtain the description information stored in the configurator. The description information may include the network configuration information, the network configuration information may include one or more of access information, an IP address of the central server, and an IP address of the printer, and the access information may include the network type and/or the IP address described. The portable patient monitor may perform the network configuration according to the network configuration information in the description information, and access to the central server or the server.

In one embodiment, the portable patient monitor may establish the connection with the configurator provided inside the ward or beside the hospital bed, obtain the network configuration information of the description information stored in the configurator, then perform network configuration according to the network type and/or the IP address described in the access information in the network configuration information, and access to a data network related to the medical area position setting information. For example, the portable patient monitor may establish the connection with a configurator (the configurator) of a hospital bed (the target object) in the target area, obtain the network type and/or the IP address described in the network configuration information of the description information stored in the configurator, then perform network configuration according to the network type and/or the IP address described in the access information in network configuration information, and access to the network for the hospital that is related to the medical area position setting information.

In one embodiment, the portable patient monitor may establish the connection with the configurator provided inside the ward or beside the hospital bed, obtain the network configuration information of the description information stored in the configurator, perform connection configuration according to the IP address of the central server in the obtained network configuration information, and access to the central server or the server related to medical area position setting information. For example, the portable patient monitor may establish the connection with the configurator (the configurator) of the hospital bed (the target object) in the target area, obtain the IP address of the central server in the network configuration information of the description information stored in the configurator, then perform connection configuration according to the obtained IP address of the central server, and access to the central server or the server related to the medical area position setting information.

In one embodiment, the portable patient monitor may establish the connection with the configurator provided in the ward or beside the hospital bed, obtain the network configuration information of the description information stored in the configurator, perform configuration according to the IP address of the printer in the obtained network configuration information, and access to the printer related to medical area position setting information. For example, the portable patient monitor may establish the connection with the configurator (the configurator) of the hospital bed (the target object) in the target area, obtain the IP address of the printer in the network configuration information of the description information stored in the configurator, then perform configuration according to the obtained IP address of the printer, and access to the printer related to the medical area position setting information.

S203: When the portable patient monitor needs to send collected physiological data to the network for the hospital, the physiological data can be sent to a network device in the network for the hospital. Alternatively, the physiological data and the medical area position setting information may also be sent to the network device such as the central server or the server in the network for the hospital together. Alternatively, the physiological data may also be sent through the network for the hospital to other network devices, such as a bedside patient monitor, a server and a printing device, in the network for the hospital. The configurator and the portable patient monitor are mechanically separated, that is, the configurator and the portable patient monitor are respectively two independent devices.

In an embodiment of this disclosure, the portable patient monitor may establish the connection with the configurator provided inside the ward or beside the hospital bed, obtain the description information of the target object stored in the configurator, and send, after completing the configuration, the physiological data and the medical area position setting information to the central server or the server when the portable patient monitor needs to send the collected physiological data of the target object (such as a patient) to the central server or the server.

Specifically, the portable patient monitor may establish the connection with the configurator provided inside the ward or beside the hospital bed, and obtain a bed number identification of the target object (such as a hospital bed), or the bed number identification and the department identification included in the medical area position setting information and the one or more network configuration information stored in the configurator. When the portable patient monitor needs to send the collected physiological data to the central server or the server, the collected monitoring data and the medical area position setting information may be processed to obtain a monitoring message, and the monitoring message may be further sent to the central server or the server. For example, the portable patient monitor may establish the connection with the configurator (the configurator) of the hospital bed in a target area, and obtain the bed number identification as No. 21 for the hospital bed (the target object) stored in the configurator (configurator), or the bed number identification of 21 and the department identification of 03 (i.e., the ear-nose-throat department) included in the medical area position setting information, and the one or more network configuration information such as the network type and/or the IP address, the IP address of the central server, and the IP address of the printer. When the portable patient monitor needs to send the collected physiological data to the central server or the server, the collected physiological data of the patient in the hospital bed and the medical area position setting information such as the hospital bed number 21 and/or the department 03, i.e., the ear-nose-throat department are sent to the central server or the server (such as a monitoring center).

In an embodiment of this disclosure, the portable patient monitor may obtain the description information, perform the network configuration according to the network configuration information in the description information, access to the central server or the server, and send the physiological data and the medical area position setting information to the central server or the server when the collected physiological data needs to be sent to the central server or the server, such that the portable patient monitor can be quickly set to adapt to the new ward, department or hospital region, can be quickly connected to the central server or the server of the new department to automatically complete the uploading of real-time and history monitoring data.

Figure 3:
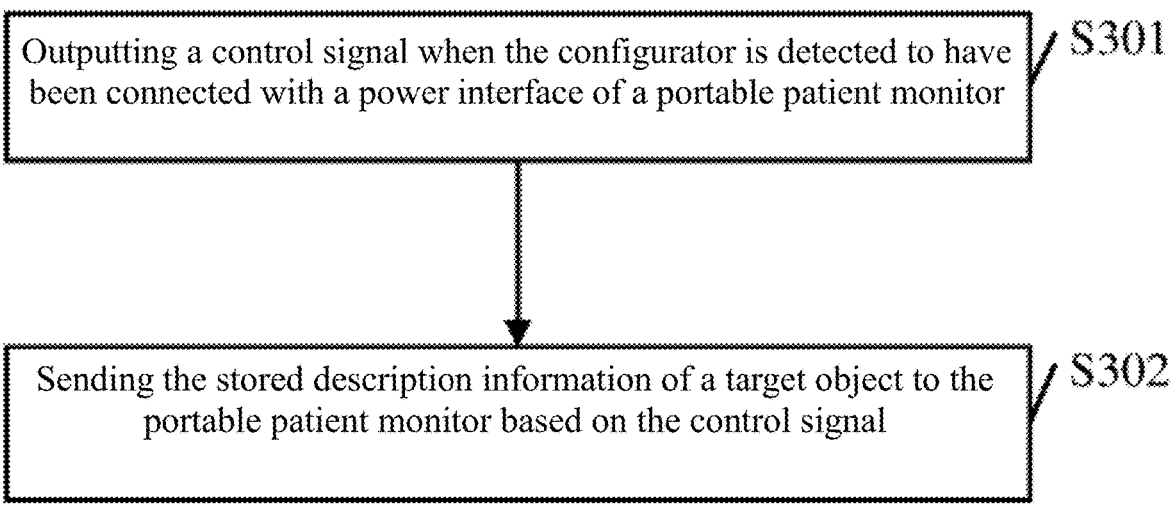
FIG. 3 is a schematic flowchart of another data transmission method provided by an embodiment of this disclosure.

Specifically, referring to FIG. 3, FIG. 3 is a schematic flow chart of another data transmission method provided by an embodiment of this disclosure. This method differs from the method embodiment of FIG. 2 in that this embodiment of this disclosure is applied to a configurator. The description of the configurator is as above. Specifically, the method of the embodiment of this disclosure may include the following steps.

At step S301, when the configurator is detected to be connected with a power interface of a portable patient monitor, a control signal may be output.

In an embodiment of this disclosure, the configurator may detect whether power conduction is established between the configurator and the portable patient monitor, and output the control signal when it is detected that the configurator and the portable patient monitor are electrically connected with each other. Specifically, in the embodiment of this disclosure, the configurator may include a first power interface and a second power interface. The configurator may be connected to the commercial power via the first power interface and to an external power interface provided on the portable patient monitor via the second power interface, and output the control signal when the configurator is detected to be electrically connected with the portable patient monitor.

At step S302, the stored description information of a target object may be sent to the portable patient monitor based on the control signal.

In an embodiment of this disclosure, the configurator may send the stored description information of the target object to the portable patient monitor based on the control signal, such that the portable patient monitor can perform data update and network configuration according to the description information. Specifically, the configurator can store the description information of the target object (such as a patient) in the area where it is located, output the control signal when the configurator detects the operation of electrically conduction, and send the stored description information of the target object to the portable patient monitor based on the control signal.

In an embodiment of this disclosure, the configurator may establish a power connection with the portable patient monitor, and output the control signal, and the configurator may be controlled to send the stored description information of the target object to the portable patient monitor based on the control signal, thereby ensuring that the portable patient monitor is configured according to the obtained description information of the target object to improve the accuracy of the configuration of the portable patient monitor.

Figure 4:
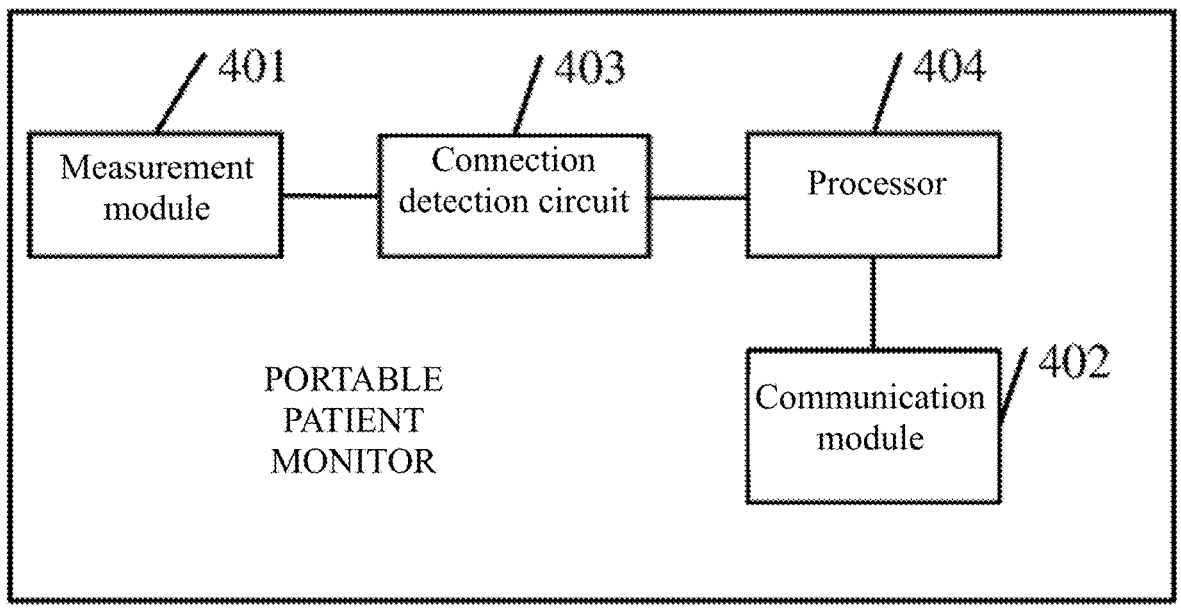
FIG. 4 is a schematic structural diagram of a portable patient monitor provided by an embodiment of this disclosure.

Specifically, referring to FIG. 4, FIG. 4 is a schematic structural diagram of a portable patient monitor provided by an embodiment of this disclosure. As shown in the figure, the portable patient monitor in this embodiment may include: a measurement module 401, a communication module 402, a first connection detection circuit 403 and a processor 404.

The measurement module 401 may be used for collecting physiological data of a patient.

The communication module 402 may be used for accessing to a network for a hospital and performing data transmission of the physiological data.

The first connection detection circuit 403 may be used for outputting a control signal after detecting that the portable patient monitor has been connected to a configurator, where the configurator and the portable patient monitor are mechanically separated.

The processor 404 may be used for obtaining description information from the configurator based on the control signal, and configuring the portable patient monitor according to the obtained description information, where the description information may include at least one of network configuration information and medical area position setting information.

In an embodiment of this disclosure, the portable patient monitor may collect the physiological data of the patient, output the control signal after detecting that the portable patient monitor has been connected to the configurator, obtain the description information from the configurator based on the control signal, perform configuration on the portable patient monitor according to the obtained description information, and access to the network for the hospital to perform data transmission of the physiological data.

Figure 5:
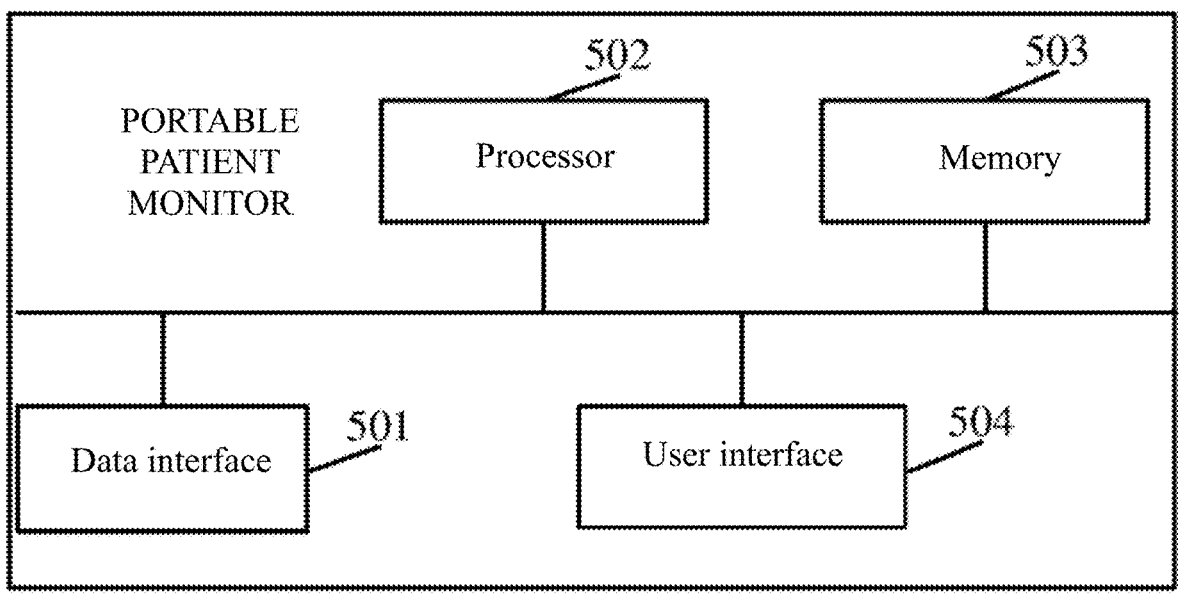
FIG. 5 is a schematic structural diagram of another portable patient monitor provided by an embodiment of this disclosure.

Specifically, referring to FIG. 5, FIG. 5 is a schematic structural diagram of another portable patient monitor provided by an embodiment of this disclosure. As shown in the figure, the portable patient monitor in this embodiment may include: one or more data interfaces 501, one or more processors 502 and a memory 503, where the data interface 501, the processor 502 and the memory 503 can be connected to each other, the memory 503 can be used for storing instructions, and the processor 502 can be used for executing the instructions stored in the memory 503. The memory 503 can be used for storing a computer program that may include program instructions, and the processor 502 may be configured to invoke the program instructions to perform the following steps.

Description information may be obtained, where the description information may refer to the descriptions above.

Network configuration may be performed according to network configuration information in the description information, and a central server or the server may then be accessed.

When the collected physiological data needs to be sent to the central server or the server, the physiological data and medical area position setting information can be sent to the central server or the server.

In one of the embodiments, the portable patient monitor may also use the structure as described above, referring to the foregoing for details.

The processor 502 of the portable patient monitor may be further configured to invoke the program instructions to perform the following steps.

Description information may be obtained, where the description information may include network channel configuration information that can communicate with a bedside patient monitor.

Network configuration may be performed according to the communication channel configuration information in the description information, and communication channel may be established with the bedside patient monitor.

Through the communication channel established with the patient monitor, data stream about the above-mentioned physiological data and settings or control information issued by the patient monitor can be transmitted.

It should be understood that in the embodiments of this disclosure, the processor 502 may be a central processing unit (CPU), and the processor may also be another general-purpose processor, a digital signal processor (DSP), an application specific integrated circuit (ASIC), a field-programmable gate array (FPGA), or another programmable logic device, discrete gate or transistor logic device, discrete hardware component, etc. The general-purpose processor may be a microprocessor, or the processor may be any conventional processor.

The data interface 501 may include a touch panel, a microphone, etc., and the user interface 504 may include a display (LCD, etc.), a loudspeaker.

The memory 503 may include a read-only memory and a random access memory, and provide instructions and data to the processor 502. Part of the memory 503 may further include a nonvolatile random access memory. For example, the memory 503 may also store device type information.

In the specific implementation, the data interface 501, the processor 502, and the memory 503 described in the embodiment of this disclosure can perform the implementation of the data transmission method described in the embodiment of FIG. 2 provided by an embodiment of this disclosure, and can also perform the implementation of the portable patient monitor described in the embodiment of the present invention, and details are not described herein again.

In an embodiment of this disclosure, the portable patient monitor may obtain the description information, perform network configuration according to the network configuration information in the description information, access to the central server or the server, and send the physiological data and the medical area position setting information to the central server or the server when the collected physiological data needs to be sent to the central server or the server, such that the portable patient monitor can be quickly set to adapt to the new ward, department or hospital region, and can be quickly connected to the central server or the server of the new department, to automatically complete the uploading of real-time and history monitoring data.

Figure 6:
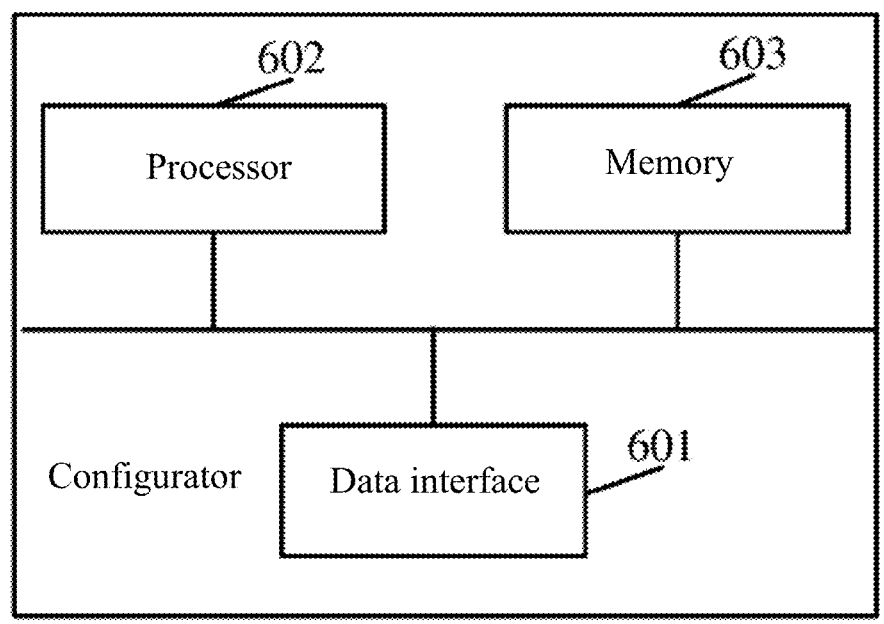
FIG. 6 is a schematic structural diagram of a configurator provided by an embodiment of this disclosure.

Specifically, referring to FIG. 6, FIG. 6 is a schematic structural diagram of a configurator provided by an embodiment of this disclosure. As shown in FIG. 6, the configurator in this embodiment may include: one or more data interfaces 601, one or more processors 602 and a memory 603, where the data interface 601, the processor 602 and the memory 603 may be connected to each other. The memory 603 may be used for storing instructions, and the processor 602 may be used for executing the instructions stored in the memory 603. The memory 603 may be used for storing a computer program including program instructions, and the processor 602 may be configured to invoke the program instructions to perform the following steps.

A control signal may be output when the configurator is detected to be electrically conducted with a power interface of a portable patient monitor.

The stored description information of a target object can be sent to the portable patient monitor based on the control signal.

The devices mentioned herein, such as the central server, the server, the printing device and the bedside patient monitor, which can be connected to the portable patient monitor through the network for the hospital can all be referred to as network devices in the network for the hospital.

It should be understood that in the embodiments of the present invention, the processor 602 may be a central processing unit (CPU), and the processor may also be another general-purpose processor, a digital signal processor (DSP), an application specific integrated circuit (ASIC), a field-programmable gate array (FPGA), or another programmable logic device, discrete gate or transistor logic device, discrete hardware component, etc. The general-purpose processor may be a microprocessor, or the processor may be any conventional processor, etc.

The data interface 601 may include a touch panel, a microphone, etc., and the memory 603 may include a read-only memory and a random access memory, and provide instructions and data to the processor 602. Part of the memory 603 may also include a nonvolatile random access memory. For example, the memory 603 may also store device type information.

In the specific implementation, the data interface 601, the processor 602, and the memory 603 described in the embodiment of the present invention can perform the implementation of the data transmission method described in the embodiment of FIG. 3 provided by an embodiment of the present invention, and can also perform the implementation of the portable patient monitor described in the embodiment of the present invention, and details are not described herein again.

In an embodiment of this disclosure, the output signal may be output when the configurator establishes a power connection with the portable patient monitor, and the configurator can be controlled to send the stored description information of a target object to the portable patient monitor based on the control signal, thereby ensuring that the portable patient monitor is configured according to the obtained description information of the target object to improve the accuracy of the configuration of the portable patient monitor.

Those of ordinary skilled persons in the art would have been able to understand that the implementation of all or some of the procedures of the methods in the embodiments described above could be achieved by hardware commanded by a computer program. The program can be stored in a computer-readable storage medium, and when being executed, may include the procedures of the embodiments of the methods described above. The storage medium can be a magnetic disk, an optical disc, a read-only memory (ROM), a random access memory (RAM), etc.

The disclosure above is merely preferred embodiments of the present invention, and of course, the scope of the present invention cannot be limited thereby. Therefore, equivalent changes made according to the claims of the present invention still fall within the scope of the present application.

What is claimed is:

1. A monitoring system, comprising:
a portable patient monitor; and a configurator,
wherein the portable patient monitor and the configurator are in a detachable mechanical connection with each other, and the portable patient monitor is capable of working independently after the portable patient monitor and the configurator are mechanically separated;
the configurator is used for storing description information that comprises network configuration information and position setting information;
the portable patient monitor comprises:
a measurement module that collects physiological data of a patient;
a communication module that has access to a network for a hospital and performs data transmission of the physiological data;
a first connection detection circuit that is capable of outputting a control signal after detecting that the portable patient monitor is connected with the configurator; and
a processor that obtains the description information from the configurator based on the control signal, and configures the portable patient monitor according to the obtained description information;
wherein the network configuration information comprises access information;
the portable patient monitor performs network configuration according to at least one of a network type and an IP address described in the access information, and accesses to a part of the network for the hospital that is related to the position setting information and performs data transmission of the physiological data, wherein the part related to the position setting information is at least one of a server, a central server, a printer and a bedside patient monitor;
wherein an external power interface is provided on the portable patient monitor, and the configurator further comprises:
a first power interface that connects to a commercial power; and
a second power interface that connects to the first power interface and is further capable of being connected to the external power interface provided on the portable patient monitor,
wherein the first connection detection circuit is capable of detecting the connection between the second power interface and the external power interface, and outputting the control signal when the second power interface is connected to the external power interface.

2. The monitoring system of claim 1, wherein
the network configuration information comprises an IP address of the central server; and
the portable patient monitor performs connection configuration according to the obtained IP address of the central server, and accesses to the central server that is in the network for the hospital and is related to the position setting information.

3. The monitoring system of claim 1, wherein
the network configuration information comprises an IP address of the printer; and
the portable patient monitor performs configuration according to the obtained IP address of the printer, and connects to the printer that is in the network for the hospital and is related to the position setting information.

4. The monitoring system of claim 1, wherein the physiological data comprises one or more of electrocardiogram, blood oxygen, respiration, temperature and blood pressure.

5. The monitoring system of claim 1, wherein the position setting information comprises one or more of bed number identification, department identification, hospital region identification and ward identification.

6. The monitoring system of claim 4, wherein the physiological data uploaded by the portable patient monitor comprises one or more display data and/or one or more prompt data among a physiological parameter information value, physiological parameter waveform data, physiological parameter trend waveform data, alarm data, an alarm prompt message, trend alarm information and early warning data.

7. The monitoring system of claim 1, wherein the configurator is fixed inside a ward or beside a hospital bed.

8. The monitoring system of claim 1, wherein a battery module is provided on the configurator or the portable patient monitor.

9. The monitoring system of claim 1, wherein
the network configuration information comprises network channel configuration information for establishing communication between the portable patient monitor and a bedside patient monitor; and
the processor obtains the network channel configuration information from the configurator based on the control signal, and configures the communication module of the portable patient monitor according to the obtained network channel configuration information, thereby establishing a communication channel between the portable patient monitor and the bedside patient monitor.

10. A portable patient monitor, comprising:
a measurement module that collects physiological data of a patient;
a communication module that accesses to a network for a hospital and performs data transmission of the physiological data to at least one of a server, a central server, a printer and a bedside patient monitor;
a first connection detection circuit that is capable of outputting a control signal after detecting that the portable patient monitor has been connected to a configurator, wherein the configurator and the portable patient monitor are mechanically separated; and
a processor that obtains description information from the configurator based on the control signal, and performs configuration on the portable patient monitor according to the obtained description information, wherein the description information comprises network configuration information and position setting information;
wherein an external power interface is provided on the portable patient monitor, and the configurator further comprises:
a first power interface that connects to a commercial power; and
a second power interface that connects to the first power interface and is further capable of being connected to the external power interface provided on the portable patient monitor, wherein the first connection detection circuit is capable of detecting the connection between the second power interface and the external power interface, and outputting the control signal when the second power interface is connected to the external power interface.

* * * * *